(12) United States Patent
Cooper

(10) Patent No.: US 6,332,884 B1
(45) Date of Patent: Dec. 25, 2001

(54) TWO PHASE THERMALLY DEFORMABLE BIOCOMPATIBLE ABSORBABLE POLYMER MATRIX FOR USE IN MEDICAL DEVICES

(75) Inventor: Kevin Cooper, Warren, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/497,060

(22) Filed: Feb. 2, 2000

Related U.S. Application Data

(62) Division of application No. 09/055,342, filed on Apr. 6, 1998, now abandoned.

(51) Int. Cl.$^7$ .............................. A61F 2/28; A61F 2/44; A61B 17/56; A61B 17/58
(52) U.S. Cl. ................. 606/77; 606/230; 623/1.38; 623/11; 623/12; 623/16; 623/17; 525/411; 525/415
(58) Field of Search .............................. 623/1.38, 11, 12, 623/16, 17; 606/77, 78, 230; 525/411, 415

(56) References Cited

U.S. PATENT DOCUMENTS

| | | | |
|---|---|---|---|
| 4,810,775 | 3/1989 | Bendix et al. | 528/480 |
| 4,844,854 | 7/1989 | Kaplan et al. | 264/235 |
| 5,080,665 | 1/1992 | Jarrett et al. | 606/219 |
| 5,124,103 | 6/1992 | Kaplan et al. | 264/102 |
| 5,320,624 | 6/1994 | Kaplan | 606/77 |
| 5,376,102 | 12/1994 | Jarrett et al. | 525/415 |
| 5,569,250 | 10/1996 | Sarver et al. | 606/69 |
| 5,641,501 | 6/1997 | Cooper et al. | 424/426 |
| 5,714,159 | 2/1998 | Shalaby | 424/426 |

FOREIGN PATENT DOCUMENTS

| | | | |
|---|---|---|---|
| 2079274 | 3/1993 | (CA) | C08L/67/04 |
| 0707044 | * 4/1996 | (EP) . | |

* cited by examiner

*Primary Examiner*—Patricia A. Short

(57) ABSTRACT

An absorbable biocompatible polymeric matrix is described. The matrix has a continuous phase that is preferably amorphous. The matrix also has a disperse phase of low melting biocompatible material that acts as scattering centers for light and melts at a temperature lower than the continuous phase of the matrix. This matrix is especially useful in a variety of medical devices. When this matrix is heated to about the melting temperature of the dispersed phase the matrix undergoes a visual change. This provides a visual cue to a surgeon using the medical devices as to when the device can be safely shaped or manipulated without imparting undue stress to the device. As the medical device cools below the temperature at which it may be safely deformed the matrix resumes its original appearance signalling that it may no longer be safely shaped or manipulated.

7 Claims, 1 Drawing Sheet

TWO PHASE THERMALLY DEFORMABLE BIOCOMPATIBLE ABSORBABLE POLYMER MATRIX FOR USE IN MEDICAL DEVICES

This is a Divisional of prior application No. 09/055,342, filed Apr. 6, 1998 now abandoned.

FIELD OF THE INVENTION

The general field to which the invention relates to is devices made of absorbable polymer matrices. Specifically, absorbable polyester matrices for use in a thermally deformable plating system for the fixation of bone and cartilage, especially hard tissue of the cranium.

BACKGROUND OF THE INVENTION

Synthetic absorbable biocompatible polymers are well known in the art. Such polymers are typically used to manufacture medical devices, which are implanted in body tissue and absorb over time. Synthetic absorbable biocompatible polymers include homopolymers, copolymers (random, block, segmented and graft) of monomers such as glycolic acid, glycolide (d, l, meso and mixtures thereof), lactic acid, lactide, $\epsilon$-caprolactone, trimethylene carbonate and p-dioxanone. Numerous U.S. Patents describe these polymers including U.S Pat. No. 5,431,679; 5,403,347; 5,314,989; 5,431,679; 5,403,347; and 5,502,159.

There is a constant need in this art for new polymer compositions having improved physical properties when molded or extruded into medical devices and further having excellent in vivo properties. For example, it is known that copolymers of lactide and glycolide have good in vivo properties (U.S. Pat. No. 5,569,250). These materials are also generally known in the art to be single phase, amorphous or semi-crystalline copolymers with melting points exceeding 100° C., and no low melting or immiscible component.

Heat deforming of absorbable devices, such as plates, has also been described in U.S. Pat. No. 5,569,250. However, one drawback of such devices is their lack of a visual cue to aid the surgeon in knowing the precise time that they can begin deforming the device. This is critical to the device, because premature bending or otherwise manipulating it before it has relaxed (i.e., heated above its Tg or Tm) can cause stresses to form in the part, weakening it, especially in clinical situations.

Unfortunately, U.S. Pat. No. 5,569,250 does not recognize that absorbable plates, rods and pins, for example, could be manufactured from a polymeric material that provides a visual cue to a surgeon during surgery to assist him/her in appropriately applying the device to the surgical site.

Therefore, what is needed in this art is a novel device that provides a visual cue during its application (i.e., deformation during heating) to indicate when it can be safely manipulated or shaped.

The surgical devices of the present invention provide a visual cue to surgeons indicating when the surgical device may be contoured or shaped.

SUMMARY OF THE INVENTION

We have discovered an absorbable polymeric matrix that provides a visual cue when heated that the absorbable polymeric matrix may be deformed without significantly reducing the strength (due to internal stress concentration) of a device made from the polymeric matrix. These polymeric matrices are especially well suited for use in implantable surgical devices such as plates, pins, rods and the like that need to be shaped during medical procedures to accommodate the patient. The method of shaping a surgical article containing these absorbable polymeric matrices comprises heating the surgical article until a visual cue is provided by the absorbable polymeric matrix that the portion of the surgical article made from the absorbable polymeric matrix may be safely shaped, then shaping that portion of the surgical article to the desired final shape and allowing the surgical article to cool.

The foregoing and other features and advantages of the invention will become more apparent from the following description and accompanying examples.

DETAILED DESCRIPTION OF THE INVENTION

Figure 1:
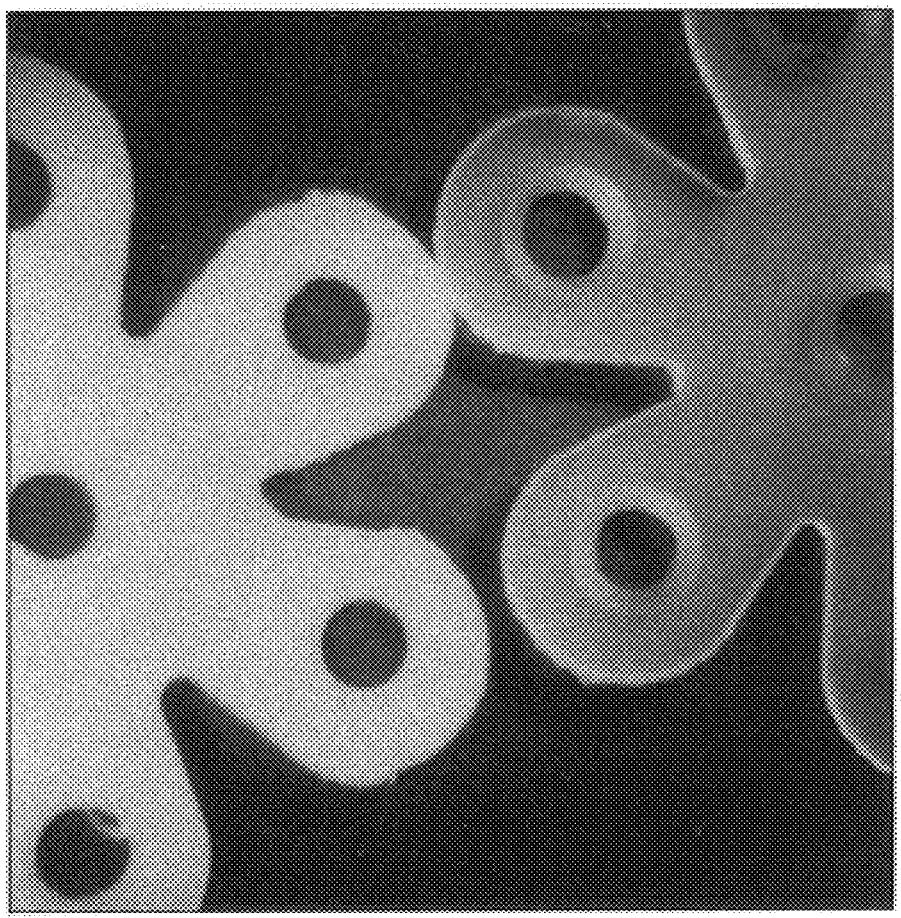
FIG. 1 photographically illustrates the visual cue of the device of the present invention. The burr hole cover plate on the left is opaque at room temperature, while the plate on the right has been heated to 55° C. is nearly transparent.

The biocompatible polymeric materials described herein are matrices having a continuous phase and a disperse phase. The continuous phase is generally composed of an amorphous biocompatible polymeric material. The dispersed phase is composed of a biocompatible material with a low melting point. The dispersed phase is believed to provide scattering centers in the matrix that when heated become transparent. This provides the surgeon a visual cue of when to bend and shape the medical device formed from the matrix. In applications that require shaping the device, such as cranial plating over a variety of bony contours, the present invention is far superior to the devices disclosed in the prior art.

The polymeric materials of the present invention are formed of a polymeric matrix with a continuous phase and a dispersed phase of a lower melting crystalline material forming a second distinct phase. The continuous phase is preferably formed from amorphous biocompatible polymers. Suitable amorphous biocompatible polymers include, but are not limited to, amorphous aliphatic ester polymers selected from the group consisting of amorphous polylactide (including D-lactide, L-lactide, mixtures of D-lactide and L-lactide, as well as, lactic acid polymers), amorphous polyglycolide (including polyglycolic acid polymers), amorphous poly-1,4-dioxan-2-one, amorphous polytrimethylene carbonate (also known as poly-1,3-dioxan-2-one) and copolymers and blends thereof. For crystalline compositions the polymers will have a melting point above 80° C. and most preferably above 70° C.

The dispersed phase is a semi-crystalline polymer that will form a separate phase in the continuous matrix and melt at a temperature between about 40° C. to about 65° C., and most preferably will melt at a temperature in the range of from about 40° C. to about 55° C. Suitable absorbable biocompatible polymers that may used especially in association with the aliphatic ester polymers listed for the dispersed phase include, but are not limited to, biocompatible absorbable polymers selected from the group consisting of poly($\epsilon$-caprolactone); copolymers of $\epsilon$-caprolactone and with up to 40 mole percent of a second monomer selected from the group consisting of lactide (lactic acid), glycolide (glycolic acid), 1,4-dioxan-2-one, and trimethylene carbonate; and copolymers of $\epsilon$-caprolactone or trimethylene carbonate with greater than 60 mole percent 1,4-dioxan-2-one, but less than 90 mole percent.

Additionally, the dispersed phase may be formed from low melting biocompatible organic molecules of an appropriate size to act as scattering sites that may be blended with the matrix without adversely affecting the chemical or mechanical properties of the matrix polymer for its intended use. One suitable organic material is polyethylene glycol (PEG).

Additionally, the continuous phase and the dispersed phase could also be provided by using block copolymers composed of the continuous phase and dispersed phase polymers described above, provided that the block copolymers formed two distinct phases, wherein the dispersed phase block forms scattering sites and the dispersed phase has a melting point in the temperature range previously described.

Generally, the amount of biocompatible material in the dispersed phase will be that amount sufficient to provide a visual cue when the biocompatible materials in the dispersed phase become transparent or melt or otherwise visually changes during heating of the device. By way of a guideline, but not limiting the scope of the present invention, for the combination of the continuous phase aliphatic polyesters previously listed with the dispersed phase biocompatible absorbable polymers previously listed, it is preferred that the weight percent of dispersed polymer comprise in the range of from about 1 to about 50 and most preferable from about 2 to about 20. The weight percentages being based on the total weight percent of the matrix polymers equaling 100 percent.

In a medical procedure the device will be shaped to accommodate the patients individual anatomy or the particular surgical requirements. The medical device would be heated preferably in a liquid media until the medical device provides a visible cue that it may be shaped (without imparting undue stress to the medical device). In one preferred embodiment of the present invention when heated the absorbable polymer matrices under goes a reversible visual change when a substantial amount of the dispersed polymer phase becomes clear by melting. The scattering sites when transparent no longer scatter light and the absorbable polymeric matrix will appear clear as long as the dispersed phase remains above its melting point. For the absorbable polymeric matrix described above the surgeon would heat the matrix to a temperature from about 40° C. to about 65° C. until it becomes nearly transparent. While the matrix appears clear the surgeon will be able to safely shape the device.

The polymers of the present invention will typically be synthesized in a ring opening polymerization. That is, the aliphatic lactone monomers lactide, glycolide, ε-caprolactone, p-dioxanone, and trimethylene carbonate are polymerized in the presence of an organometallic catalyst and an initiator at elevated temperatures. The organometallic catalyst is preferably tin based, e.g., stannous octoate, and is present in the monomer mixture at a molar ratio of monomer to catalyst ranging from about 10,000/1 to about 100,000/1. The initiator is typically an alkanol (including diols and polyols), a glycol, a hydroxyacid, or an amine, and is present in the monomer mixture at a molar ratio of monomer to initiator ranging from about 100/1 to about 5000/1. The polymerization is typically carried out at a temperature range from about 80° C. to about 240° C., preferably from about 100° C. to about 220° C., until the desired molecular weight and viscosity are achieved.

The polymer blends of the present invention are manufactured in a conventional manner, preferably in the following manner. The homopolymers and copolymers, prepared as described above, are individually charged into a conventional mixing vessel or reactor vessel having a conventional mixing device mounted therein, such as an impeller or equivalents thereof. Then, the polymers and copolymers are mixed at a temperature of about 100° C. to about 230° C., more preferably from about 160° C. to about 200° C., for about 5 to about 90 minutes, more preferably for about 10 to about 45 minutes, until a uniformly dispersed polymer blend is obtained. Then, the polymer blend is further processed by removing it from the mixing device, cooling to room temperature, grinding, and drying under pressures below atmospheric at elevated temperatures for a period of time using conventional apparatuses and processes.

Additionally, a minor amount (less than 5, preferably less than 3 weight percent weight percent) of additional lactone monomers selected from the group consisting of 1,3-dioxan-2-one, p-dioxanone, delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 6,6-dimethyl-dioxepan-2-one, 6,8-dioxabicycloctane-7-one and combinations of two or more thereof may be added.

Under the above described conditions, the polymers and blends composed of glycolide,ε-caprolactone, p-dioxanone, lactide and trimethylene carbonate will typically have a weight average molecular weight of about 20,000 grams per mole to about 300,000 grams per mole, more typically about 40,000 grams per mole to about 200,000 grams per mole, and preferably about 60,000 grams per mole to about 150,000 grams per mole. These molecular weights provide an inherent viscosity between about 0.5 to about 4.0 deciliters per gram (dL/g), more typically about 0.7 to about 3.5 dL/g, and most preferably about 1.0 to about 3.0 dL/g as measured in a 0.1 g/dL solution of hexafluoroisopropanol (HFIP) at 25° C. Also, it should be noted that under the above described conditions, the residual monomer content would be less than about 5 weight percent.

Articles such as medical devices are molded from the polymers and blends of the present invention by use of various injection and extrusion molding equipment equipped with dry nitrogen atmospheric chamber(s) at temperatures ranging from about 100° C. to about 230° C., more preferably 140° C. to about 200° C., with residence times of about 1 to about 20 minutes, more preferably about 2 to about 10 minutes.

The polymers and blends of the present invention can be melt processed by numerous methods to prepare a vast array of useful devices. These materials can be injection or compression molded to make implantable medical and surgical devices, including wound closure devices. The preferred devices are orthopedic plates, pins and rods.

Alternatively, the blends and polymers can be extruded to prepare fibers. The materials of the present invention may also be spun as multifilament yarn and woven or knitted to form sponges or gauze, (or non-woven sheets may be prepared) or used in conjunction with other molded compressive structures such as prosthetic devices within the body of a human or animal where it is desirable that the structure have high tensile strength and desirable levels of compliance and/or ductility. Useful embodiments include tubes, including branched tubes, for artery, vein or intestinal repair, nerve splicing, tendon splicing, sheets for tying up and supporting damaged surface abrasions, particularly major abrasions, or areas where the skin and underlying tissues are damaged or surgically removed. Additionally, the polymers and blends can be molded to form films which, when sterilized, are useful as adhesion prevention barriers.

In another embodiment of the present invention, the polymers and blends can be used as a drug delivery matrix. To form this matrix, the polymer would be mixed with a therapeutic agent. The variety of different therapeutic agents that can be used in conjunction with the polymers of the present invention is vast. In general, therapeutic agents which may be administered via the pharmaceutical compositions of the invention include, without limitation: antiinfectives such as antibiotics and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

The drug delivery matrix may be administered orally, parenterally, subcutaneously, vaginally or anally. Matrix formulations may be formulated by mixing one or more therapeutic agents with the polymer. The therapeutic agent, may be present as a liquid, a finely divided solid, or any other appropriate physical form. Typically, but optionally, the matrix will include one or more additives, such as diluents, carriers, excipients, stabilizers or the like.

The amount of therapeutic agent will depend on the particular drug being employed and medical condition being treated. Typically, the amount of drug represents about 0.001% to about 70%, more typically about 0.001% to about 50%, most typically about 0.001% to about 20% by weight of the matrix.

The quantity and type of polymer incorporated into the drug delivery matrix will vary depending on the release profile desired and the amount of drug employed.

Upon contact with body fluids, the polymer undergoes gradual degradation (mainly through hydrolysis) with concomitant release of the dispersed drug for a sustained or extended period. This can result in prolonged delivery (over, say 1 to 5,000 hours, preferably 2 to 800 hours) of effective amounts (say, 0.0001 mg/kg/hour to 10 mg/kg/hour) of the drug. This dosage form can be administered as is necessary depending on the subject being treated, the severity of the affliction, the judgment of the prescribing physician, and the like.

Following this or similar procedures, those skilled in the art will be able to prepare a variety of formulations.

Furthermore, the polymers and blends of the present invention can be processed by conventional techniques to form foams, which are useful as hemostatic barriers, bone substitutes, and tissue scaffolds.

In more detail, the surgical and medical uses of the filaments, films, foams and molded articles of the present invention include, but are not necessarily limited to knitted products, woven or non-woven, and molded products including:

a. burn dressings
b. hernia patches
c. medicated dressings
d. fascial substitutes
e. gauze, fabric, sheet, felt or sponge for liver hemostasis
f. gauze bandages
g. arterial graft or substitutes
h. bandages for skin surfaces
i. burn dressings
j. bone substitutes
k. needles
l. intrauterine devices
m. draining or testing tubes or capillaries
n. surgical instruments
o. vascular implants or supports
p. vertebral discs
q. extracorporeal tubing for kidney and heart-lung machines
r. artificial skin and others
s. stents
t. suture anchors
u. injectable defect fillers
v. preformed defect fillers
w. tissue adhesives and sealants
x. bone waxes
y. cartilage replacements
z. hemostatic barriers
aa. tissue scaffolds
bb. monofilament and braided sutures
cc. orthopedic, spinal and nuerosurgical plates, rods and pins.

The following non-limiting examples are illustrative of the principles and practice of this invention. Numerous additional embodiments within the scope and spirit of the invention will become apparent to those skilled in the art.

EXAMPLES

The examples describe an opaque plating system that comprises a polymer or polymer blends that when heated is transparent then opaque again upon cooling to body temperature.

In the synthetic process, the high molecular weight aliphatic polyesters are prepared by a method consisting of reacting lactone monomers via a ring opening polymerization at temperatures of 100° C. to 230° C. for 2 to 24 hours under an inert nitrogen atmosphere until the desired molecular weight and viscosity are achieved.

In the blending process, the polymer blends of the present invention are prepared by individually charging the synthesized aliphatic homo- and co-polyesters into a conventional mixing vessel. The homopolymers and copolymers are mixed at a temperature of 100° C. to 230° C., for 5 to 90 minutes until a uniformly dispersed polymer blend is obtained.

In the examples which follow, the blends, polymers and monomers were characterized for chemical composition and purity (NMR, FT-IR), thermal analysis (DSC), melt rheology (melt stability and viscosity), molecular weight (inherent viscosity), and baseline mechanical properties (Instron stress/strain).

Inherent viscosities (I.V., dL/g) of the blends and polymers were measured using a 50 bore Cannon-Ubbelhode dilution viscometer immersed in a thermostatically controlled water bath at 25° C. utilizing chloroform or HFIP (hexafluoroisopropanol) as the solvent at a concentration of 0.1 g/dL.

Several examples will be described in the following few pages. Parts and percentages where used are parts and percentages as specified as weight or moles.

Example 1

Synthesis of a 85:15 (mol/mol) poly(lactide-co-glycolide) copolymer

The method described below and utilized in this example is similar to those described in U.S. Pat. Nos. 4,643,191, 4,653,497, 5,007,923, 5,047,048 which are incorporated by reference, and is known to those skilled in the art.

To a flame dried 500 mL 1-neck round bottom flask equipped with an overhead mechanical stirrer and nitrogen inlet, 268 grams (1.86 moles) of L(−) lactide, 38.4 grams (0.330 moles) of glycolide, 0.53 grams ($7 \times 10^{-3}$ moles) of glycolic acid initiator, and 131 microliters of a 0.33 M solution of stannous octoate catalyst were added.

The assembly was then placed in a high temperature oil bath at 185° C. The stirred monomers quickly began to melt. The low viscosity melt quickly increased in viscosity. Mechanical stirring of the high viscosity melt was continued for a total reaction time of 4 hours.

The 85:15 (mol/mol) poly(lactide-co-glycolide) copolymer was removed from the bath, cooled to room temperature under a stream of nitrogen, isolated and ground. The polymer was then dried under vacuum at 110° C. for 24 hours. Inherent viscosity using HFIP as a solvent was 1.90 dL/g.

Example 2

Synthesis of a 95:5 (mol/mol) poly($\epsilon$-caprolactone-co-p-dioxanone) copolymer The method described below in this example is similar to those described in U.S. Pat. Nos. 4,643,191, 4,653,497, 5,007,923, 5,047,048 which are incorporated by reference, and is known to those skilled in the art.

To a flame dried 500 mL 1-neck round bottom flask equipped with an overhead mechanical stirrer and nitrogen inlet, 262.43 grams (2.3 moles) of $\epsilon$-caprolactone, 12.38 grams (0.12 moles) of p-dioxanone, 0.84 grams (0.011 moles) of glycolic acid initiator, and 147 microliters of a 0.33 M solution of stannous octoate catalyst were added.

The assembly was then placed in a high temperature oil bath at 190° C. The stirred monomers quickly began to melt. The low viscosity melt quickly increased in viscosity. Mechanical stirring of the high viscosity melt was continued for a total reaction time of 24 hours.

The 95:5 (mol/mol) poly($\epsilon$-caprolactone-co-p-dioxanone) copolymer was removed from the bath, cooled to room temperature under a stream of nitrogen, isolated and ground.

The polymer was then dried under vacuum at 40° C. for 24 hours. Inherent viscosity using HFIP as a solvent was 1.77 dL/g.

Example 3

Blending of a 85:15 (mol/mol) poly(lactide-co-glycolide) copolymer with a 95:5 (mol/mol) poly($\epsilon$-caprolactone-co-p-dioxanone) copolymer at a blended weight ratio of 95:5

29.45 grams of a 85:15 (mol/mol) poly(lactide-coglycolide) prepared as described in Example 1 was melt blended with 1.55 grams of the 95:5 (mol/mol) poly($\epsilon$-caprolactone-co-p-dioxanone) copolymer of Example 2 at a weight ratio of 95:5 in a Brabender Plasti-corder mixer at a temperature of 170° C. for 23 minutes. The resulting blend was removed from the Brabender mixer, cooled, ground and dried under vacuum at 50° C. for 24 hours. Inherent viscosity using HFIP as a solvent was 1.90 dL/g.

Example 4

Blending of a 85:15 (mol/mol) poly(lactide-co-glycolide) copolymer with a 95:5 (mol/mol) poly($\epsilon$-caprolactone-co-p-dioxanone) copolymer at a blended weight ratio of 80:20

24.8 grams of a 85:15 (mol/mol) poly(lactide-co-glycolide) prepared as described in Example 1 was melt blended with 6.2 grams of the 95:5 (mol/mol) poly($\epsilon$caprolactone-co-p-dioxanone) copolymer of Example 2 at a weight ratio of 80:20 in a Brabender Plasti-corder mixer at a temperature of 170° C. for 23 minutes. The resulting blend was removed from the Brabender mixer, cooled, ground and dried under vacuum at 50° C. for 24 hours. Inherent viscosity using HFIP as a solvent was 1.83 dL/g.

Example 5

Blending of a 85:15 (mol/mol) poly(lactide-co-glycolide) copolymer with a 95:5 (mol/mol) poly($\epsilon$-caprolactone-co-p-dioxanone) copolymer at a blended weight ratio of 60:40

18.6 grams of a 85:15 (mol/mol) poly(lactide-co-glycolide) prepared as described in Example 1 was melt blended with 12.4 grams of the 95:5 (mol/mol) poly($\epsilon$caprolactone-co-p-dioxanone) copolymer of Example 2 at a weight ratio of 60:40 in a Brabender Plasti-corder mixer at a temperature of 170° C. for 23 minutes. The resulting blend was removed from the Brabender mixer, cooled, ground and dried under vacuum at 50° C. for 24 hours. Inherent viscosity using HFIP as a solvent was 1.80 dL/g.

Example 6

Synthesis of a 60:40 (mol/mol) poly($\epsilon$-caprolactone-co-L-lactide) copolymer The method described below in this example is similar to those described in U.S. Pat. Nos. 4,643,191, 4,653,497, 5,007,923, 5,047,048 which are incorporated by reference, and is known to those skilled in the art.

To a flame dried 500 mL 1-neck round bottom flask equipped with an overhead mechanical stirrer and nitrogen inlet, 165.75 grams (1.45 moles) of $\epsilon$-caprolactone, 139.68 grams (0.97 moles) of L-lactide, 0.84 grams (0.011 moles) of glycolic acid initiator, and 147 microliters of a 0.33 M solution of stannous octoate catalyst are added.

The assembly is then placed in a high temperature oil bath at 190° C. The stirred monomers quickly began to melt. The low viscosity melt quickly increased in viscosity. Mechanical stirring of the high viscosity melt is continued for a total reaction time of 24 hours.

The 60:40 (mol/mol) poly($\epsilon$-caprolactone-co-L-lactide) copolymer is removed from the bath, cooled to room temperature under a stream of nitrogen, isolated and ground. The polymer is then dried under vacuum at 40° C. for 24 hours. Inherent viscosity using HFIP as a solvent is 1.92 dL/g.

Example 7

Injection molding a circular plate (of FIG. 1) of a blend of 85:15 poly(lactide-co-glycolide) copolymer and 95:5 poly($\epsilon$caprolactone-co-p-dioxanone) copolymer at a blended weight ratio of 95:5

1.5 Kg of a blend as formed in Example 3 was added to a nitrogen purged hopper of a 28 ton Engel injection molder equipped with an 18 mm diameter barrel to form a circular plate as shown in FIG. 1. Three heating zones of 180, 170, and 140° C. were employed to melt the blend as it entered the barrel. A nozzle temperature of 185° C. with an injection pressure of 700 psi and a speed of 2 in/s were used to feed the molten material down the barrel. Each injection produced a single part in a single cavity mold. A temperature of 45° C. was used in the mold to optimize the stress levels in the part. Using this process 2 parts are formed per minute.

Example 8

A circular burr hole cover plate (as illustrated in FIG. 1) was manufactured from the matrix described in Example 3 by the injection molding process described in Example 7. The plate was then immersed in a vessel containing a biocompatible heat transfer medium (i.e. warm water, . . . ) at a temperature of about 50–60° C., until the plate became clear. This visual cue signals the surgeon that the plate may be removed from the vessel and shaped by bending it without causing damage to the plate. The surgeon would then secure the plate to a fracture site in a conventional manner using conventional fasteners (i.e. rivets, pins and screws)

I claim:

1. A method of shaping a surgical article having a portion thereof formed from an absorbable polymeric matrix, said matrix comprising a continuous phase and a dispersed phase of a crystalline or semi-crystalline material that has a melting temperature lower than the melting temperature of said continuous phase and that forms a distinct phase that provides a visual cue upon melting of said material, the method comprising: heating that portion of the surgical article that is formed from the absorbable polymeric matrix to a minimum temperature that is at least about the melting temperature of the material and is effective to provide said visual cue to a maximum temperature of about 65° C., shaping that portion of the surgical article to the desired final shape while the visual cue is present; and allowing the surgical article to cool.

2. The process of claim 1 wherein the surgical article is heated to a temperature in the range of from about 40° C. to about 65° C.

3. The process of claim 1 wherein the surgical article is heated in a biocompatible liquid medium.

4. The process of claim 1 wherein the surgical article is selected from the group consisting, bone substitutes, vertebral discs, pins, rods and plates.

5. The process of claim 1 wherein the continuous phase comprises an amorphous aliphatic polyester selected from the group consisting of amorphous polylactide, amorphous polyglycolide, amorphous poly-1,4-dioxan-2-one, amorphous polytrimethylene carbonate and miscible blends thereof.

6. The process of claim 5 wherein the dispersed phase comprises an aliphatic polyester selected from the group consisting of poly($\epsilon$-caprolactone); copolymers of $\epsilon$-caprolactone and with up to 40 mole percent of a second monomer selected from the group consisting of lactide, lactic acid, glycolide, glycolic acid, 1,4-dioxan-2-one, and trimethylene carbonate; copolymers of $\epsilon$-caprolactone or trimethylene carbonate with greater than 60 mole percent 1,4-dioxan-2-one but less than 90 mole percent and blends thereof.

7. The process of claim 6 wherein the dispersed phase comprises from about 2 to about 20 weight percent of the absorbable polymeric matrix.

* * * * *